United States Patent

Favonio

[11] Patent Number: 5,975,898
[45] Date of Patent: Nov. 2, 1999

[54] SIMPLIFIED VALVE ACTUATING DEVICE FOR DENTAL EQUIPMENT

[75] Inventor: Angelo Favonio, Vimercate (Milan), Italy

[73] Assignee: Faro Fabbrica Apparecchiature Razionali Odontoiatriche S.p.A., Ornago, Italy

[21] Appl. No.: 09/122,997

[22] Filed: Jul. 28, 1998

[30]     Foreign Application Priority Data

Jul. 28, 1997  [IT]  Italy ................................. MI97A1796

[51] Int. Cl.⁶ ......................................................... A61C 1/02
[52] U.S. Cl. ............................................. 433/98; 433/101
[58] Field of Search ............................. 433/98, 99, 100, 433/101; 137/240, 606

[56]              References Cited

U.S. PATENT DOCUMENTS

| | | | |
|---|---|---|---|
| 3,474,816 | 10/1969 | Burgess | 137/240 |
| 3,476,153 | 11/1969 | Roland | 433/101 |
| 4,201,051 | 5/1980 | Hall | 433/101 |
| 4,304,251 | 12/1981 | Schadel et al. | 137/240 |
| 4,443,195 | 4/1984 | Matsui | 433/98 |
| 4,450,862 | 5/1984 | Hogan | 137/595 |
| 4,797,098 | 1/1989 | Kawata | 433/98 |
| 4,894,010 | 1/1990 | Castellini | 433/101 |
| 5,074,787 | 12/1991 | Tsukada | 433/98 |
| 5,800,170 | 9/1998 | Tsukada | 433/98 |

FOREIGN PATENT DOCUMENTS 229406  7/1960  Australia .................................. 433/98

*Primary Examiner*—John J. Wilson
*Assistant Examiner*—Patrick A. Hilsmier
*Attorney, Agent, or Firm*—Oblon, Spivak, McClelland, Maier & Neustadt, P.C.

[57]              ABSTRACT

A pneumatically operated, simplified valve actuating device for dental equipment, the valve being capable of avoiding an undesirable dripping of dental instruments at the end of the work. The device includes a valve actuating element identified in a four-way valve, whose body includes a housing for a piston connected to a bobbin, wherein said casing is on one side connected to a selector unit and on the other side to a one-way retention valve, capable of receiving pressurized air from a reducer unit and passing it from said selector unit to a constantly pressurized air line coming directly from said reducer unit and to at least one dental instrument.

10 Claims, 5 Drawing Sheets

SIMPLIFIED VALVE ACTUATING DEVICE FOR DENTAL EQUIPMENT

BACKGROUND OF THE INVENTION

1. Field of the Invention

This invention refers to a simplified valve actuating device for dental equipment.

2. Discussion of the Background

Dental equipment presently in use are provided with a device that prevents the dental instruments from dripping at the end of the work.

This device is based on a technique of aspirating the last drop by creating a suction effect. The suction effect occurs by using a membrane-type valve, which aspirates the last drop inside the last section of the flow duct provided in the instrument. This action suffices to prevent, by capillary action, any loss of fluids from the instrument itself.

A device as described above is presently no longer allowed, as the aspiration outlined above may lead to a contamination of the water network as well as of the equipment, instruments and accessories by bacteria or viruses.

A number of alternative systems have been provided, which consist in removing this last drop to the outside by an impulse or blow of timed and controlled compressed air.

To achieve this, some complex electronic equipment has been developed, capable of applying such a control by eliminating the last water drop by a compressed air blow.

However, it is in any case necessary to prevent the dripping or loss of liquids from such dental instruments at the end of the work, even in the case of using some totally pneumatic, non-electronic dental equipment.

The general scope of this invention is to solve the technical problem evidenced in the field by purely pneumatic means, by eliminating the mentioned drawbacks of the known art, in an extremely simple, economical and particularly functional manner.

Another scope is to produce a general solution capable of being advantageously used in any type of dental instrument or assembly.

In view of the mentioned purposes it was planned, in accordance with this invention, to produce a simplified valve actuating device for dental equipment, possessing the characteristics best described in the accompanying claims.

BRIEF DESCRIPTION OF THE DRAWINGS

The structural and functional characteristics of this invention and its evident advantages in relation to the known art will become even clearer and more evident from an examination of the following description, referred to the accompanying drawings, which show a simplified valve actuating device for dental equipment according to this invention.

In these drawings:

FIG. 1a shows the position, in a side elevation view, that the pedal in FIG. 1 may assume;

FIG. 2a shows the position, in a side elevation view, that the pedal in FIG. 2 may assume;

DESCRIPTION OF THE PREFERRED EMBODIMENTS

Figure 1:
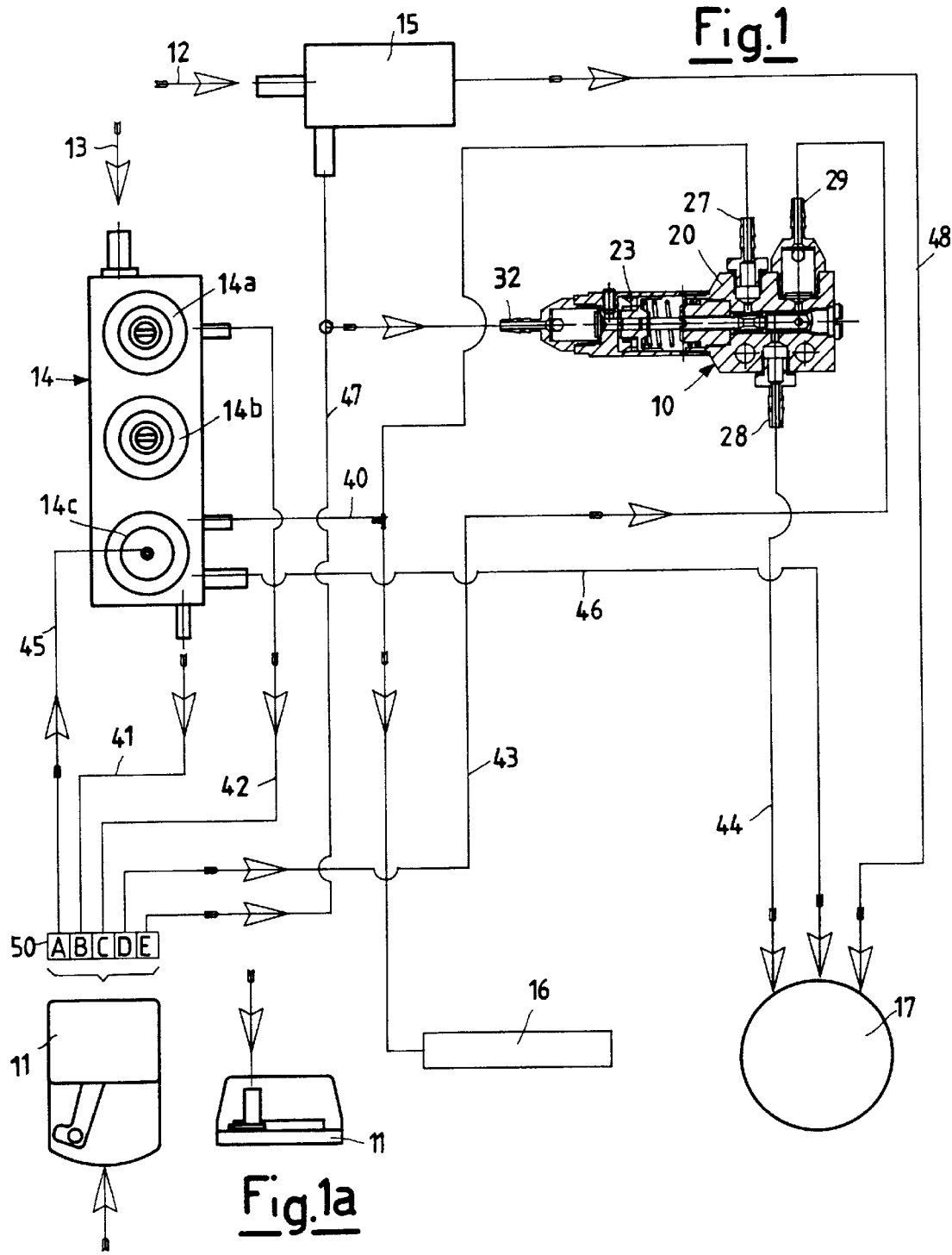
FIG. 1 is a general functional diagram of a dental equipment operated by a pedal, in which a simplified valve actuating device according to this invention is inserted in a first operating position.

With reference to the drawings, it can be noted that the simplified valve actuating device for dental equipment object of this invention can be inserted and become part of a dental equipment unit or of a so-called "dental assembly".

In the example shown, the valve actuating system inserted in a dental equipment comprises a valve element 10, a control pedal 11, as shown in the general functional diagram of the FIGS. 1, 1a and 2, 2a, as well as the various sources and utilities.

The drawing of the equipment in fact shows that the same is served by such sources as a water feed 12 at 2 bar and an air feed 13 at 6 bar, such as a compressor, capable of supplying the equipment as required.

The air feed 13 at 6 bar is connected by a reducer unit 14 to fit the various utilities and needs respect to the pressures required by the mentioned valve element 10, the pedal 11, the piloting system of a water-opening valve 15, a preselecting control 16 and various instruments, shown in a simplified manner and exemplified in 17. The reducer unit 14 provides for a reduction to 3 bar 14a, a reduction to 5 bar 14b and a proportional valve 14c.

The valve element 10 of the device is actuated, as mentioned, by the pedal 11 which determines, in its various positions, a different feed of air with the consequent piloting of even the feed of water used in the entire dental equipment. The pedal 11 can both be shifted and lowered (FIGS. 1a and 2a), while a selector unit 50 connected to the reducer unit 14 and to the various utilities 10, 15, 16 is provided in the example with at least 5 control selectors indicated by A, B, C, D and E.

Figure 3:
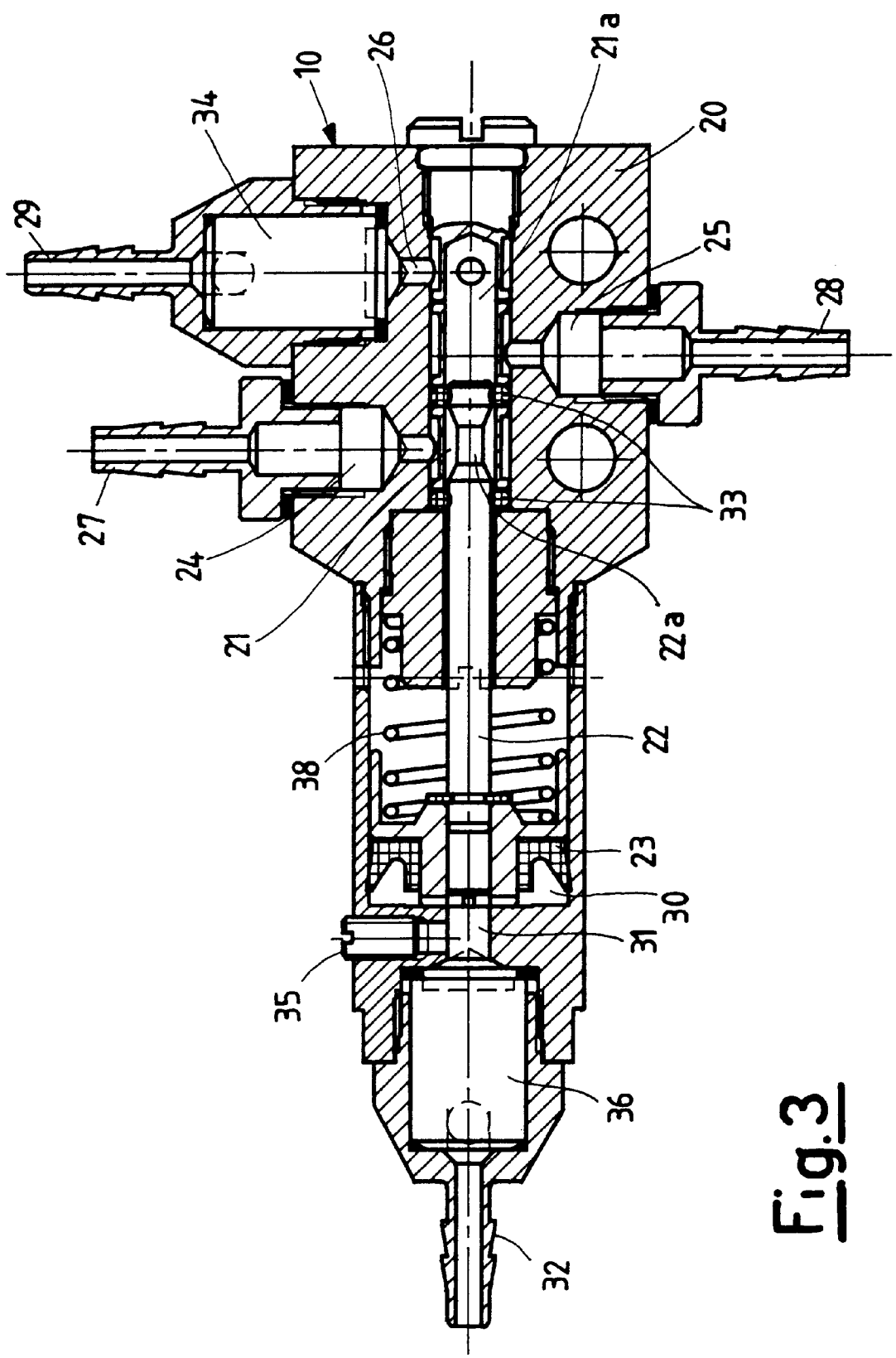
FIG. 3 is an enlarged section of the valve element as part of the simplified valve actuating device of the invention, in a resting position or delivering position of a controlled volume of cleaning air.

FIG. 3 shows the resting position, in a cross-sectional view, of the valve element 10 according to the invention, set into a first arrangement.

In this position, the valve element 10, which can be like to a four-way valve, consists of a body 20 containing a housing 21 with a bobbin 22 which is rigidly connected to an actuating piston 23, thus forming a pneumatic piston-type valve.

The bobbin 22 rigidly connected to the piston 23 is pushed by a spring 38 to an extremity of the chamber 30, thus separating the conduits 25 and 26 from a conduit 24 which can be connected to an equal number of openings 27, 28 and 29, shown as simplified fittings for quick couplings.

This chamber 30 is in turn opened toward the outside of the body 20 by a conduit 31, a one-way valve 36 and its relative opening 32 or quick coupling.

Figure 4:
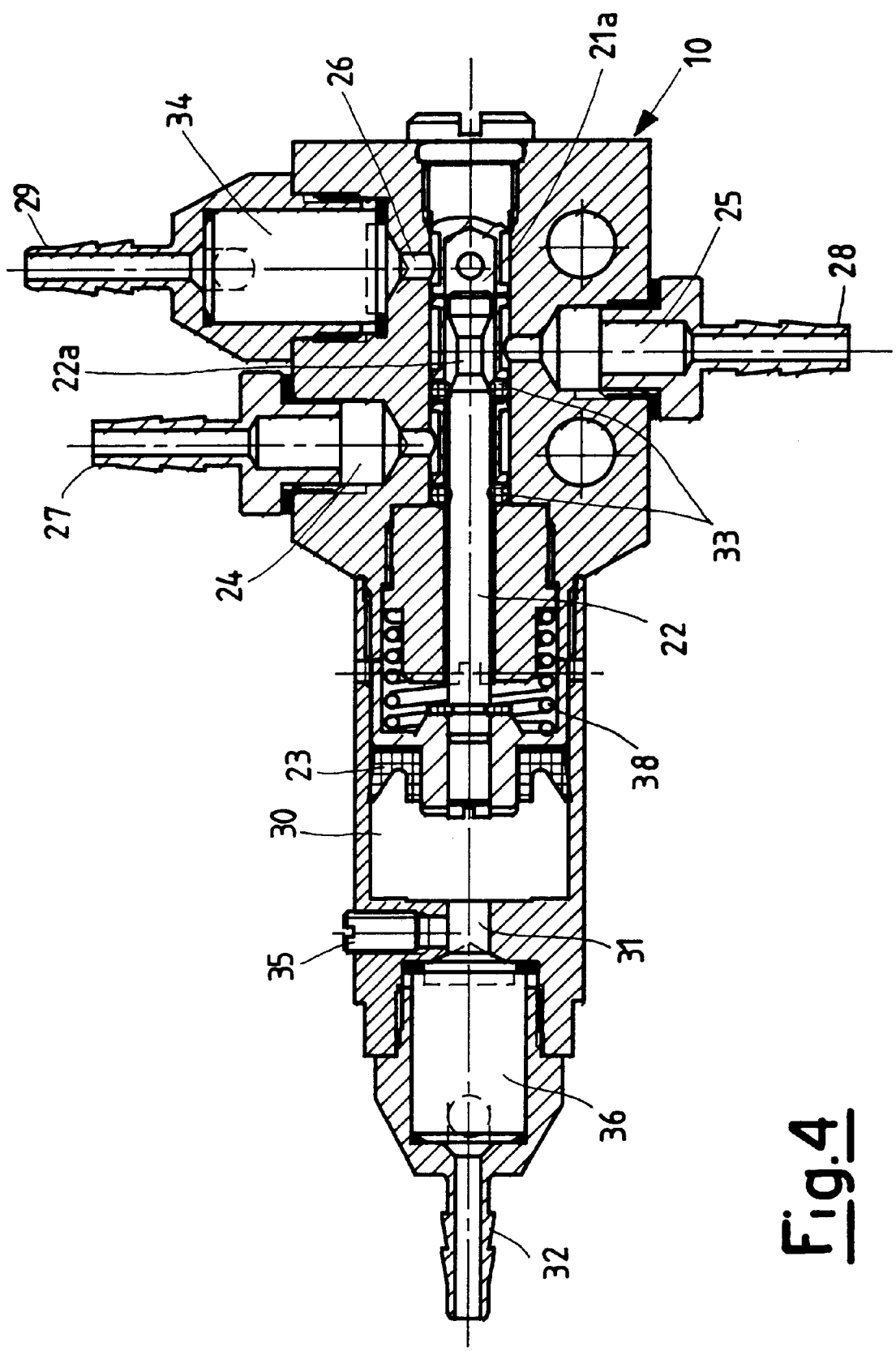
FIGS. 4 and 5 are cross-sections similar to that of FIG. 3, showing the valve element in a spray-actuating and in a closed position while eliminating the last produced drop, thanks to the previous closing of the spray.

The bobbin 22 is appropriately contoured so as to achieve a sealed closing action in its seat 21, provided with O-type sealing elements 33, in a first resting position and while delivering a controlled volume of cleaning air (chip), and in a second spray-actuating position as shown in FIGS. 3 and 4.

The body of the bobbin 22 further provides for a section of smaller diameter 22a which allows to eliminate the produced drop, while actuating the closing, thanks to a previous closing of the spray-actuating control.

A one-way retention valve 34 is also provided at the conduit 26 of the opening 29, which is normally kept open by gravity or by the action of a spring, not shown.

The operation of such a simplified valve element 10 inserted into any dental equipment and controlled by the pedal 11 is described at this point, so as to also provide a better understanding of the whole structure of the valve actuating device.

As already mentioned, in the position shown in FIG. 3 this valve element 10 is continuous connected by the opening 27 and a relative line 40 to the reducer unit 14 of the air feed 13 at the proportional valve 14c. This line 40 always holds air at a pressure of 5 bar. It should also be kept in mind that the reducer unit is always connected by a line 41 at 5 bar and a line 42 at 3 bar to the selector unit 50 of the pedal 11, all this of course only after the dental equipment has been switched on.

FIG. 3 shows a second condition or delivering position for the controlled dosage of cleaning air, the so-called "chip".

In this position, from the reducer unit 14, a pressure on the pedal 11 as shown in FIG. 1a, in addition to injecting the air of the line 40 at a pressure of 5 bar, also actuates further connections.

A control selector B actuated by the pedal 11 in fact connects the line 41, by the same selector unit 50 and a further control selector D, to a line 43 connected to the opening 29 of the valve element 10.

Because the piston 23 and the bobbin 22 are in the previously indicated position, the air entering from the opening 29 and freely crossing the retention valve 34 passes into the conduit 26 and moves on from the terminal area or extremity 21a of the housing 21 to the conduit 25 and from there to the opening 28. This opening 28 leads through a line 44 to the instruments 17.

This generates the feed of a controlled volume of cleaning air to the instrument 17. The release of the pedal 11 determines the stoppage of this flow of cleaning air.

FIGS. 1 and 3 show that in a resting position, after delivering the controlled volume and the closing of this controlled feed, the valve element 10 of the invention is always in the same position, identical to the original or to the closed position.

This resting position may also be one which comes into being at any instant during the use of the equipment, if the operator has not held it necessary to use any water in the instruments.

Figure 2:
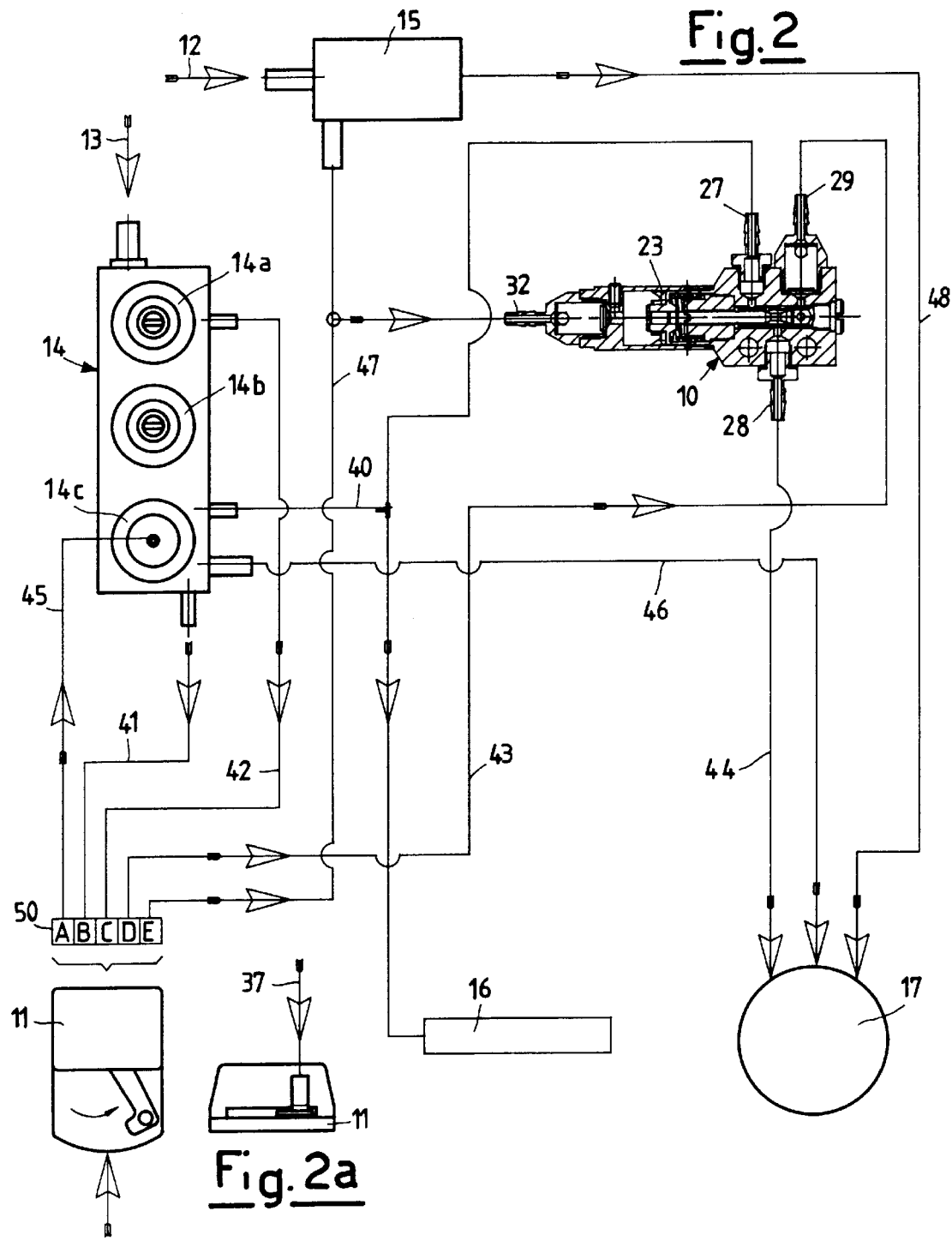
FIG. 2 is a diagram similar to that in FIG. 1, in a different operating position.

The operator now shifts the pedal 11 into the position of FIGS. 2, 2a, thus achieving a position of the valve element 10 as shown in FIG. 4.

It must immediately be emphasized that in this position the selector group 50 activates all its control selectors by connecting the line 41 at 5 bar using the control B to a control A. The control A activates a line 45 that returns to the reducer unit 14, and from there moves the air at 5 bar, through a line 46, directly to the instrument 17.

Moreover, the control C connects the line 42 at 3 bar to both the controls D and E. The control D activates a connection identical to that previously described, using the line 43 and the openings 29 and 28 to reach the instrument 17. Other than in the previous phase, this control does not feed air at 5 bar, but at 3 bar, and actuates the spraying function for the instrument.

On the other hand, the control E connects a line 47 which actuates the water-opening valve 15, thus allowing the flow of water at 2 bar to the instrument 17 through a line 48.

Moreover, the air at 3 bar enters through the opening 32 into the valve element 10, so as to push the piston 23 toward the opposite end of the chamber 30. This shifting of the piston 23 involves a simultaneous shifting of the rigidly connected bobbin 22 toward the extremity 21a of the housing 21. Before this operating phase and during the actuating and setting-up phase of the equipment, a plug valve 35 facing toward the outside of the chamber 30 has been adjusted. In this manner the volume of the air discharged from the chamber at the return motion of the piston can be adjusted, thus regulating the time needed to return the valve to its resting position.

Once the spray has been effected by releasing the pedal 11 in a direction opposite to that shown by the arrow 37 in FIG. 2a, a few other controls are released by the selector unit 50 of the pedal 11, i.e. the controls D and E. The opening of the water valve 15 ends, thus instantly blocking the water without generating suction. This also stops the feed of air at 3 bar toward the opening 32 in the valve element 10 acting against the piston 23.

The only continuing action is the flow of air at 5 bar from the opening 27 of the valve element 10, while the spring 38 restarts the return motion of the piston 23 and tends to push it toward its resting position (FIG. 3).

This shifting motion allows the air arriving from the opening 27 to enter the extremity 21a of the housing 21. Moreover, the air also moves toward the conduit 26 and closes the retention valve 34.

Figure 5:
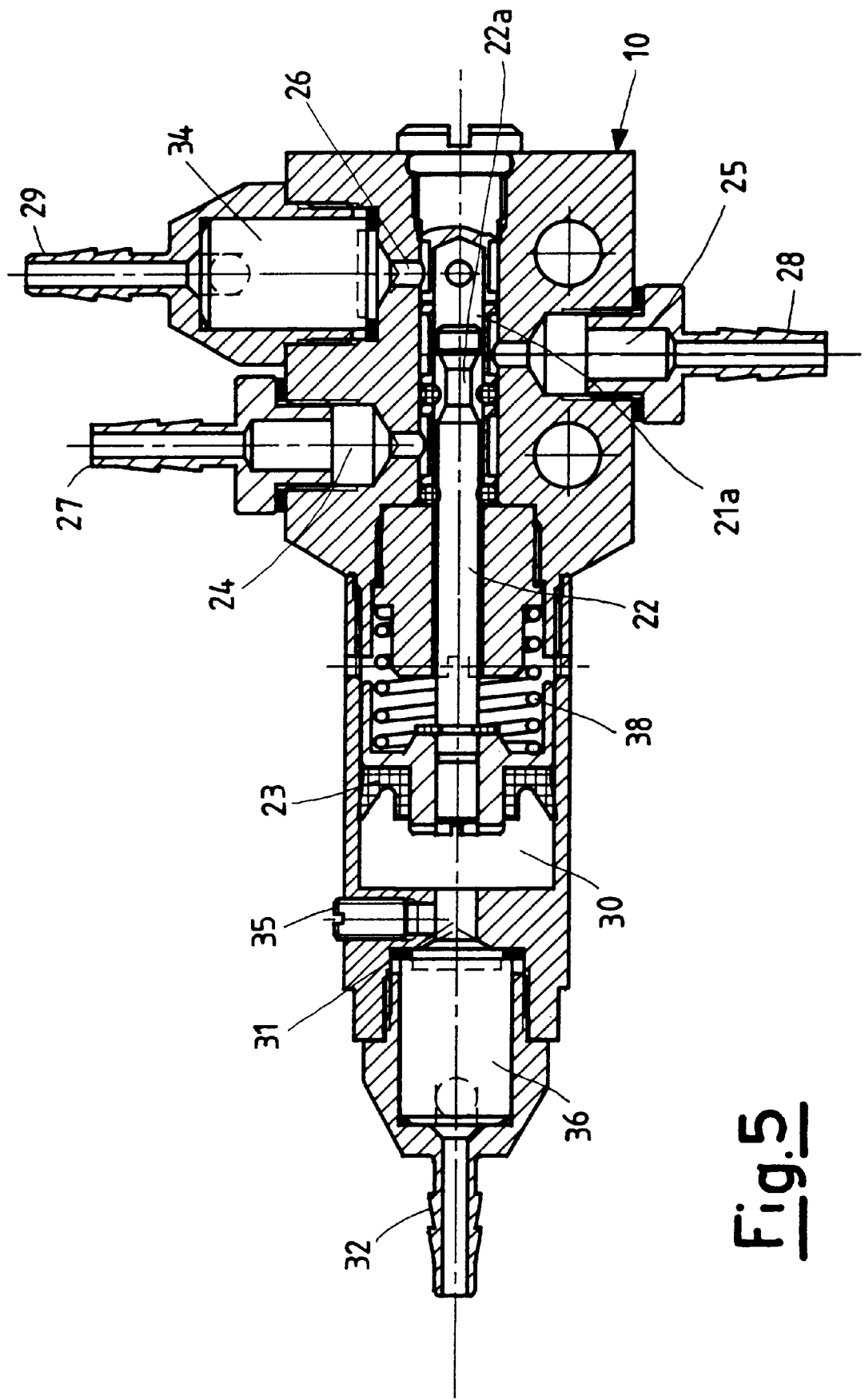

FIG. 5 illustrates this constantly evolving and moving situation.

The air also pushes the bobbin 22 by acting on its extremity and on the portion of a smaller diameter 22a.

In this manner the one-way valve 36 keeps the air inside the chamber 30 and the adjustable vent governs the return time of the piston 23 by keeping the opening 27, which is connected by the housing 21 to the opening 28, connected to the instrument 17.

This achieves the feeding of pressurized air at 5 bar toward the instrument 17, thus cleaning out, aspirating and expelling the last drop of residual water that cannot be left inside the equipment.

The elimination of the residual water can be carried out by the final air nozzle or in the same way by using a second nozzle provided for the purpose in the dental equipment.

This produces the emission of a flow of air at 5 bar capable of being regulated both in volume and in expulsion time. This is in fact made possible both in the operating phase of the valve element 10 of this invention by acting on the adjustment of valve 35, and in the construction phase by appropriately enlarging the extremities 21a of the housing. In this second case it is in fact possible to establish a certain capability depending on the dental equipment to be used and to build valve elements of a different type, suitable for different types of equipment.

The valve element 10 is then brought to the position shown in FIG. 3, which also corresponds to the resting position after a spray-type actuating phase.

This, like the resting position after an injection of a controlled volume of cleaning air (chip), is also a normal position in which the equipment may find itself during operation, and in which the user may encounter the equipment.

The type of technical solution proposed by the invention is evident from the foregoing description referring to the figures.

In this way, the scopes mentioned in the premise of this description are achieved.

Of course, the embodiments of the device may differ from those shown only for exemplifying and non-limiting purposes in the drawings.

The scope of the protection of this invention is in any case outlined by the accompanying claims.

I claim:

1. Valve actuating device for dental equipment, which comprises:

a source of pressurized air, a source of pressurized water, a reducer unit for the pressurized air, a control pedal with at least five control selectors and a valve element, said selectors being communicated with said reducer unit, to a selector unit of said pedal and to at least one dental instrument by connecting lines wherein said valve element comprises a four-way valve which controls air flow at a first pressure and at a second pressure, said second pressure being less than said first pressure, said valve having within a body a portion thereof a housing having a piston located therein which is connected to a bobbin, said housing being connected at a first side thereof to said selector unit and at a second side thereof to a first one-way retention valve which allows communication of pressurized air from said reducer unit at the second pressure to said valve element by flowing of the pressurized air from said selector unit to a constantly pressurized air line communicated in the said reducer unit, and from said selector unit to at least one dental instrument which is attached to said valve element and wherein the water pressure source is communicated with said valve element and said four way valve includes a second one-way retention valve for control of air flow at said second pressure.

2. Valve actuating device for dental equipment according to claim 1, wherein a portion of said housing releases a pre-selected volume of air toward the outside and is adjustable by a plug valve facing said portion of the housing.

3. Valve actuating device for dental equipment according to claim 1, which comprises an air line controlling said piston, said air line being connected to a water opening valve toward at least one of said dental instruments.

4. Valve actuating device for dental equipment according to claim 1, wherein in a spraying phase of said at least one instrument of said dental equipment, said pedal is positioned in such a manner that a selector unit thereof connects air lines thereof to entrance openings in said valve element, an exit opening in said valve element and a proportional valve of said reducer using additional lines, and being also connected to said instrument, and being actuated by piloting air exiting from said selector unit and arriving at a water opening valve.

5. Valve actuating device for dental equipment according to claim 4, wherein in a subsequent closing phase of said spraying phase, said pedal shifts said selector unit so as to close off said lines between said reducer unit opening and said instrument, so that air remaining inside a chamber facing an adjusting valve exits and determines a connection between said opening connected to said reducer unit and said opening connected to said at least one instrument while emitting air for a certain period of time determined by the calibration of said adjusting valve.

6. Valve actuating device for dental equipment according to claim 5, wherein said bobbin is provided at one extremity with a portion of a smaller diameter which, during closing operation, eliminates a produced drop from exiting, as a result of previous closing of the spray-actuating phase.

7. Valve actuating device for dental equipment according to claim 1, wherein said piston is housed in a chamber located at an extremity of said housing facing said conduit and said opening, said piston, while shifted inside said chamber at the extremity turned toward said housing compressing a spring so as to start a subsequent returning motion.

8. Valve actuating device for dental equipment according to claim 1, wherein said openings comprise fittings for quick couplings.

9. Valve actuating device for dental equipment according to claim 1, wherein said pedal is controlled so as to be shiftable as well as being raised or lowered and wherein said selector unit connected to said reducer unit and to various utilities is provided with at least five control selectors.

10. Valve actuating device for dental equipment according to claim 1, wherein said pressurized air source comprises a compressor.

* * * * *